United States Patent
Saber

(10) Patent No.: US 11,389,561 B2
(45) Date of Patent: *Jul. 19, 2022

(54) METHODS FOR APPLYING A SKIN TREATMENT

(71) Applicant: DIRECT COMPONENTS, INC., Cheyenne, WY (US)

(72) Inventor: Shien-Lin Saber, Laguna Beach, CA (US)

(73) Assignee: DIRECT COMPONENTS, INC., Cheyenne, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,381

(22) Filed: Nov. 7, 2016

(65) Prior Publication Data
US 2017/0049925 A1    Feb. 23, 2017

Related U.S. Application Data

(63) Continuation-in-part of application No. 14/337,098, filed on Jul. 21, 2014, now Pat. No. 9,511,034.

(60) Provisional application No. 61/913,821, filed on Dec. 9, 2013.

(51) Int. Cl.
| | | |
|---|---|---|
| A61L 26/00 | (2006.01) | |
| A61K 9/70 | (2006.01) | |
| A61Q 19/08 | (2006.01) | |
| A61K 8/25 | (2006.01) | |
| A61K 8/892 | (2006.01) | |
| A61K 8/891 | (2006.01) | |
| A61K 8/58 | (2006.01) | |
| A61K 8/894 | (2006.01) | |
| A61K 8/895 | (2006.01) | |
| A61Q 19/00 | (2006.01) | |

(52) U.S. Cl.
CPC ............ *A61L 26/0019* (2013.01); *A61K 8/25* (2013.01); *A61K 8/58* (2013.01); *A61K 8/891* (2013.01); *A61K 8/892* (2013.01); *A61K 8/894* (2013.01); *A61K 8/895* (2013.01); *A61K 9/7015* (2013.01); *A61L 26/0004* (2013.01); *A61L 26/0052* (2013.01); *A61Q 19/00* (2013.01); *A61Q 19/08* (2013.01); A61K 2800/594 (2013.01); A61K 2800/882 (2013.01); A61K 2800/884 (2013.01); A61K 2800/95 (2013.01)

(58) Field of Classification Search
CPC ............ A61L 26/0052; A61L 26/0004; A61L 26/0019; A61K 9/0019; A61K 8/892; A61K 8/25; A61K 8/894; A61K 8/58; A61K 8/891; A61K 8/895; A61K 9/7015; A61K 2800/594; A61K 2800/884; A61K 2800/882; A61K 2800/95; A61Q 19/00; A61Q 19/08

See application file for complete search history.

(56) References Cited

U.S. PATENT DOCUMENTS

| | | | |
|---|---|---|---|
| 8,691,202 B2 | 4/2014 | Yu et al. | |
| 9,511,034 B1* | 12/2016 | Garrett | ................ A61K 8/25 |
| 2004/0175414 A1* | 9/2004 | Berlat | ............. A61L 26/0004 |
| | | | 424/445 |
| 2006/0216318 A1* | 9/2006 | Majmudar | ........... A61K 9/0014 |
| | | | 424/401 |
| 2008/0226577 A1* | 9/2008 | L'Alloret | ............. A61K 8/891 |
| | | | 424/70.12 |

FOREIGN PATENT DOCUMENTS

WO    WO-2011003054 A2 *    1/2011    ............. C08L 83/04

OTHER PUBLICATIONS

ELMERS <http://www.wsc.edu/facility_services/msds/stix_all.pdf> (Year: 2011).*

M. Lis et al. "Polymers in Biology and Medicine" in Polymer Science: A Comprehensive Reference 2012 (Siloxane Polymers). (Year: 2012).*

* cited by examiner

*Primary Examiner* — Blessing M Fubara

(74) *Attorney, Agent, or Firm* — SoCal IP Law Group LLP; Brian S. Tamsut; Steven C. Sereboff

(57) ABSTRACT

The inventive subject matter provides kits, compositions and methods for treating or covering skin using a polymerizable formulation. The polymerizable formulation can include a first component including a siloxane polymer and a catalyst, and a second component including a siloxane polymer and a cross-linker. The first and second components, when combined, can form a film or seal having an elasticity that at least one of decreases the formation of fibroblasts, presses down blisters, decreases a biochemical cascade that promotes scar formation, compresses skin, and holds skin in a desired configuration.

8 Claims, No Drawings

METHODS FOR APPLYING A SKIN TREATMENT

This application is a continuation-in-part of U.S. patent application Ser. No. 14/337,098, filed on Jul. 21, 2014, which claims the benefit of priority to U.S. Provisional Application No. 61/913,821, filed on Dec. 9, 2013. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is skin treatment and coverage.

BACKGROUND

The background description includes information that may be useful in understanding the present invention. It is not an admission that any of the information provided herein is prior art or relevant to the presently claimed invention, or that any publication specifically or implicitly referenced is prior art.

Different materials with adhesive backings have been used to provide a protective barrier between the environment and various skin injuries such as burns, scars, cuts, blisters, scrapes and superficial wounds. Exemplary products include hydrocolloid blister pads with adhesive films, pre-formed silicone gel sheets including an adhesive backing, gel callus cushions having a central hole and an adhesive backing, and $2^{nd}$ Skin® knit pads, a breathable non-woven fabric including a medical grade adhesive, which protects blisters against rubbing and frictions.

Unfortunately, many known products have limited usefulness (e.g., are suitable only for specific types of injuries) and come in predetermined sizes and shapes. Additionally, known products can be difficult or even painful to remove, often leaving behind a sticky residue.

Some polymerizable film-forming compositions are also known in the art, although they are generally applicable and used to hide skin imperfections where there is no injury. For example, U.S. Pat. No. 8,691,202 to Yu et al. teaches cosmetic formulations that comprise a cross-linking component and a reactive reinforcing component, wherein the cross-linking component facilitates in situ cross-linking of the reactive reinforcing component such that a film is formed on the skin.

Unfortunately, Yu is apparently directed only to cosmetic compositions that reduce the appearance of skin or body imperfections such as under eye bags, sagging, uneven skin tone, redness, and wrinkles. Because Yu's contemplated uses are cosmetic in nature, only a very thin layer is applied, and there is apparently no significant structural integrity for use of Yu's composition in the context of an injury. Furthermore, many of Yu's compositions began to crack or peel within a few hours of application, and specific cleansers were used for complete removal.

Thus, there is still a need for improved kits, compositions and methods for skin treatment compositions.

SUMMARY OF THE INVENTION

The inventive subject matter comprises kits, compositions and methods for protecting a user's skin, and for treating a skin injury or imperfection using a polymerizable composition.

In order to provide compression to injured skin and reduce hypertrophic scarring, the films formed from contemplated polymerizable compositions can advantageously have sufficient elasticity such that the adhesion strength of the film is greater than the counterforce applied to the injury and skin by the film. Additionally, the film can have mechanical properties such that it does not easily tear, and can provide a protective layer to the skin for at least one day or at least two days that can be pulled off as a single piece (even after being worn for a period of at least one day, at least two days, or even three days or more).

In some aspects, methods for treating a skin injury using a polymerizable composition are provided. Contemplated methods can comprise applying a first silicone-containing elastomer component to the skin injury, applying a second silicone-containing elastomer component to the skin injury, and mixing the first and second components to form, within ten minutes, a film having a thickness and tensile strength effective to compress the user's skin and decrease formation of fibroblasts. It should be appreciated that the elastomer components could be applied to the skin and mixed directly on the skin, or the elastomer components could be mixed together prior to being applied to the skin injury, and the mixed components can be applied in a single step. In some aspects, the first and second components can be applied in substantially equal volumes (e.g., within 5 vol %, more preferably within 1 vol %), for example through a dual-chambered syringe having a mixing tip.

As used herein, the term "skin injury" includes any injury on or near the surface of the skin where tendons, muscles, ligaments, nerves, blood vessels or bone are not exposed to the environment. Exemplary skin injuries can include minor burns, superficial wounds, scars and keloids. However, it is contemplated that the polymerizable compositions presented herein could also be suitable for other types of injuries, for example, deep wounds that cut deeper than ½ inch, wherein tendons, muscles, ligaments, nerves, blood vessels or bone may be exposed to the environment through an opening in the user's skin.

The two silicone-containing elastomer components will preferably separately include a catalyst and a cross-linker such that premature curing of the polymerizable composition is avoided. For example, the first component can comprise between 0.05-0.2 wt % of a silicone platinum catalyst, between 70-90 wt % of a polydimethyl siloxane polymer and between 15-29.8 wt % fumed silica, while the second component can comprise between 70-90 wt % of a polydimethyl siloxane polymer, between 15-29 wt % fumed silica, and between 1-10 wt % of a siloxane polymer cross-linker. In some other aspects, the ingredients in a polymerizable composition can be separated into three, four, or even more components to be combined prior to use. Viewed from another perspective, the polymerizable composition (the combination of the two or more components) can comprise between 70-90 wt % (e.g., 75-85 wt %) of a siloxane polymer, between 15-29.8 wt % (e.g., 15-25 wt %) of a fumed silica, between 0.1-0.3 wt % (or between 0.025-0.1 wt %) of the catalyst, and between 0.5-5 wt % (e.g., 1-5 wt %) of a cross-linker.

When the components of the polymerizable compositions are mixed and applied to the user's skin, a film (optionally water-resistant) having a thickness and tensile strength effective to compress the user's skin can form within ten minutes, more preferably within five minutes or within two minutes, and adhere to the user's skin for a period of at least six hours. In some aspects, the polymerizable composition can include one or more adhesion promoters, optionally in synergistic amounts, to increase the adhesion time or the adhesion strength of the film to the user's skin.

In some aspects, a base composition (e.g., a mineral powder, cleanser, primer, a liquid spray, a gel) could be applied to the skin, preferably prior to application of the polymerizable composition. The base composition, the polymerizable composition (or both) can optionally include one or more of an anesthetic, an antiseptic, an adhesion promoter, a fumed silica, a botanical (e.g., chamomile, marigold, arnica, plant extract), a drug, a vitamin (e.g., ascorbic acid, retinol, niacinamide), an antipruritic, a catalyst, a haemostatic agent, and a vasoconstrictor. When included in the base composition or the polymerizable composition, the additional ingredients will in some preferred aspects not be present in an amount that significantly prolongs cure time of the polymerizable composition or decreases adhesion strength of the seal.

Contemplated polymerizable compositions, upon forming a seal in situ, will preferably be elastic or semi-elastic. For example, some contemplated compositions will have an elongation at break of at least 200%, more preferably at least 300%, and more preferably at least 400% (e.g., between 200-1000%, between 400 and 800%, between 450-600%), to allow for movement and stretching of the body without compromising the seal. Where the polymerizable compositions are used in different applications, or in areas of skin that does not require significant elasticity, it is contemplated that the polymerizable composition can have a lower elongation at break, or even be inelastic or substantially inelastic. Additionally, some preferred polymerizable compositions will have a hardness sufficient to prevent unwanted flowing of the seal. For example, some contemplated seals will have a hardness of at least 10 on the Shore 00 durometer scale, and more preferably at least 10 on the Shore A scale.

Still further, the polymerizable composition can be formulated such that the film formed can decrease formation of fibroblasts, press down blisters, or decrease a biochemical cascade that promotes scar formation. Some contemplated films can be water resistant and remain adhered to the user's skin for a period of at least 24 hours, at least 48 hours or at least 72 hours, and even through events where the skin is exposed to water (e.g., swimming, bathing, showering).

Various objects, features, aspects and advantages of the inventive subject matter will become more apparent from the following detailed description of preferred embodiments, along with the accompanying drawing figures in which like numerals represent like components.

DETAILED DESCRIPTION

The inventive subject matter provides compositions and methods for treating or covering skin by forming a thin film or seal using a composition that polymerizes in situ.

All commercially suitable polymerizable compositions are contemplated, including vinyl-based cure systems, silicone-based cure systems, peroxide-cure systems, heat cure systems, room temperature vulcanizing moisture cure systems, temperature activated systems, photoinitiated cure systems, and addition-cure systems. Additionally, all suitable polymerization reactions are contemplated, including hydrosilylation polymerization, condensation polymerization, and addition (chain-growth) polymerization (e.g., photopolymerization), and radical polymerization.

In some preferred aspects, the polymerizable composition will result in a cured film or seal having sufficient elasticity to allow the user to move around comfortably without the edges lifting, or adding to the pain or discomfort to the user.

The polymerizable composition is typically odorless, non-toxic, hypoallergenic, compatible with other treatments, bacteriostatic, non-explosive, non-temperature sensitive, and removable as a single piece, or in sections, after curing.

The polymerizable composition can comprise a one part system, for example, where the polymerizable composition is temperature or light activated. Alternatively, the polymerizable composition can comprise a multi-component (multi-part) system, for example, where a catalyst and a cross-linking component must be separated to prevent premature and undesired curing.

In some embodiments, methods for applying multi-component compositions to skin are provided. A first elastomer component including a catalyst, and a second elastomer component including a cross-linker are applied to the skin, for example over a skin injury to be treated, or a portion to be camouflaged. The first and second components are combined prior to, during or after application to form, within ten minutes (e.g., within five minutes), a polymerized water-resistant film having an elongation at break of at least 150%. The composition can additionally or alternatively include any of the components described herein, including for example, two or more adhesion promoters present in synergistic amounts with respect to adhesion of the film to the skin.

In other embodiments, kits for skin treatment or coverage are provided, which include a pre-formed polymerized composition, and a multi-component polymerizable composition. The multi-component polymerizable composition can comprise first and second silicone-containing elastomer components that separately include one or more silicone catalysts and one or more silicone cross-linkers. The first and second silicone-containing elastomer components can be formulated to, when applied between skin and the pre-formed polymerized composition, form a water-resistant film that adheres to each of the skin and the pre-formed polymerized composition within ten minutes, more preferably within five minutes. Viewed from a different perspective, methods of adhering pre-formed composition to skin are provided, which include the steps of applying first and second silicone-containing elastomer components to at least one of the pre-formed composition and the user's skin. The first and second components can be combined and positioned between the pre-formed composition and the skin to form a polymerized film, within five minutes, that adheres to each of the skin and the pre-formed composition for a period of at least 12 hours, more preferably at least 18 hours, and even more preferably at least 24 hours.

Multi-Component Systems

Some preferred polymerizable compositions comprise a multi-part elastomer system that cures at room or body temperature and includes (a) a first formulation or component including a polymer and catalyst (e.g., siloxane polymer and platinum catalyst), and (b) a second formulation or component comprising a polymer and a cross-linker. One or both of the formulations could include one or more of a filler, a thixotropic agent, a drug, a vitamin, a botanical, an adhesion promoter, a cure inhibitor to control the cure kinetics, or any multiples or combinations thereof.

Where the first and second formulations are separately packaged or contained in a dual chambered system, cross-linking can be prevented until the two components are mixed together (e.g., layered or applied as a mixture).

Polymer Component

In some contemplated embodiments, the polymer is a silicone polymer (siloxane polymer) with a polymer backbone of alternating silicone and oxygen atoms (i.e., siloxane bonds), and hydrocarbon (saturated, unsaturated, aromatic) organic side groups such as methyl, phenyl or vinyl, or a hydrogen attached to the silicon atoms. The siloxane polymer(s) can comprise between 20-100 wt %, more preferably at least 50 wt % (e.g., between 60-90 wt %), and even more preferably at least 70 wt % (e.g., between 75-85 wt %, between 78-82 wt %) of the polymerizable composition (i.e., of the combined two part formulation where the catalyst and cross-linker are combined).

Where PDMS is used, it can be a linear polymer made up of repeating Si—O—Si linkages and a reactive vinyl group on both ends of the polymer chain. There may be organic side groups such as dimethyl bonded to every silicone molecule the backbone of the polymer. Siloxane polymers can also be substituted with diphenyl, methylphenyl, trifluoropropyl, or any combination thereof. Some exemplary siloxanes include oligosiloxanes, polydimethylsiloxane (PDMS), vinyl-endblocked polydiphenyl siloxane, vinyl-endblocked polymethylphenylsiloxane, vinyl-endblocked trifluoropropyl siloxane, vinyl-endblocked polydiethyl siloxane, trimethyl-endblocked methylvinyl polydimethylsiloxane, trimethyl-endblocked methylvinyl polydiphenylsiloxane, trimethyl-endblocked methylvinyl polymethylphenylsiloxane, trimethyl-endblocked methylvinyl polytrifluoropropylsiloxane, and trimethyl-endblocked ethylvinyl polydimethylsiloxane. Contemplated siloxanes can be optically clear, non-toxic and non-flammable.

All suitable chain lengths of the siloxane polymer are contemplated, including between 10-2,500 repeating units long, between 200-1,000 repeating units long (or a molecular weight of between 20,000-32,000 Daltons), or between 300-400 repeating units long (e.g., 340-360), which equates to a molecular weight of ~26,000 Daltons.

According to another embodiment, a polymer can include a main chain formed primarily of organosiloxane units. Among the silicone compounds contemplated, some may display both curing and adhesive properties, for example depending on the proportion of silicone or whether they are used with a particular additive. It may therefore be possible to adjust the properties of said compositions according to the proposed use.

Crosslinker

In some contemplated embodiments where the polymer is a siloxane, a siloxane cross-linker such as a methyl-hydrogen cross-linker can be included. The cross-linker(s) can comprise between 0.1-50 wt %, between 0.1-10 wt %, between 2-10 wt %, and more preferably between 1-5 wt % (e.g., 2 wt %) of the polymerizable composition. An exemplary siloxane cross-linker used in some contemplated compositions is a small chain polymer that is trimethyl endblocked, making the ends of the chain non-functional. All suitable chain lengths of the cross-linker are contemplated, including for example, between 1-100 repeating units, more preferably between 1-50 units, and more preferably between 5-15 units and having a molecular weight of between 400-1,200 Daltons (e.g., 10 units wherein the molecular weight is approximately 800 Daltons). Along the backbone of the cross-linker can be reactive methyl-hydrogen side groups which can comprise between 1-99 mole %, more preferably between 20-80 mole %, and more preferably between 40-60 mole % (e.g., 50 mole %) of the cross-linker. The remaining mole % can comprise dimethyl side groups. Where each of the methyl-hydrogen side groups and the dimethyl side groups make up approximately 50 mole %, approximately half of the repeating units of the cross-linker will be dimethyl, and approximately half will be methyl hydrogen.

Other contemplated cross-linkers include hydride-endblocked polydimethylsiloxane, hydride-endblocked methylhydrogen polysiloxane, trimethyl-endblocked methylhydrogen methylvinyl polysiloxane, trimethyl-endblocked 100 mole % methylhydrogen polysiloxane, hydride-endblocked polydiphenylsiloxane, and hydride-endblocked phenylhydrogen polysiloxane.

Although the exemplary cross-linkers described above are siloxane cross-linkers, it should be appreciated that a person skilled in the art would be able to select a suitable cross-linker based on the polymer included in the polymerizable compositions.

Catalyst

The catalysts of contemplated polymerizable formulations can comprise a peroxide, platinum, tin, a combination thereof, or other suitable catalyst. An exemplary platinum catalyst for hydrosilylation reactions can comprise a complex of platinum with a vinyl siloxane acting as a ligand. An example of this is the Karstedt's catalyst. Other contemplated catalysts include, rhodium complex in vinly silicone fluid, organotin catalyst such as dibutyltin dilaurate, stannous octoate, dibutlytin diacetate, peroxide catalysts such as benzoyl peroxide, 2,4 dichlorobenzoyl peroxide, dicumyl peroxide, 2,5-Dimethyl-2,5-di(tert-butylperoxy)hexane.

The catalyst(s) can be present in the formulation in any suitable amount, for example, between 0.001-10 wt % (of the combined two part formulation where the catalyst and cross-linker are combined), more preferably between 0.01 and 1 wt %, more preferably between 0.06-0.3 wt %, and more preferably between 0.07 and 0.13 wt % (e.g., 0.1 wt %) of the polymerizable composition, and can include between 1-250 ppm, between 5-70 ppm, more preferably between 15-60 ppm (e.g., 30 ppm) of pure platinum.

The platinum catalyst (or at least a portion of the platinum catalyst) will preferably be separated from the cross-linker until placed within, or on, the injury. Alternatively or additionally, the platinum catalyst can be combined with the cross-linker no more than 5 minutes, no more than 3 minutes, and referably no more than 1 minute or 0.5 minute prior to being placed within, or on, the injury. Alternatively or additionally, the component or formulation comprising the platinum catalyst can be placed within the injury before or after the formulation or component comprising the cross-linker is placed within, or on, the injury. As discussed in more detail below, a base composition (e.g., spray) comprising the same or different catalyst could be applied prior to any of the first formulation (including the platinum catalyst) and the second formulation (including the cross-linker).

Filler

Where a filler is included in the polymerizable formulation, an exemplary filler includes amorphous fumed silica having a surface area of between 100-300 m$^2$/gram (e.g., between 150-250 m$^2$/gram, or approximately 200 m$^2$/gram). Other contemplated fillers include fumed silica with low surface area (e.g., 100 m$^2$/gram), fumed silica with high surface area (e.g., 400 m$^2$/gram), precipitated silica, diatomaceous earth, titanium dioxide, zinc oxide, barium sulfate, colloidal silica, and boron nitride.

The filler can comprise between 0-90 wt %, more preferably between 5-35 wt % and even more preferably between 10-23 wt % (e.g., 16 wt %) of the combined two part formulation where the catalyst and cross-linker are combined. The surface of the silica can be treated with trimethyl silyl groups so that it is more soluble with the polymer.

Thixotropic Additive

A suitable thixotropic additive (e.g., a compound that reduces the flowability of a material rendering it non-slump) can also be included in some contemplated polymerizable compositions in any suitable amount. For example, the thixotrope can comprise between 0.1-5 wt %, between 0.5-2.5 wt %, and more preferably between 1-2 wt % (e.g., 1.5 wt %) of the combined two part formulation where the catalyst and cross-linker are combined. An exemplary thixotrope included in some contemplated formulations is a hydroxyl endblocked polydimethyl siloxane with a chain length of between 10-20 repeating units (e.g., 15 repeating units with a molecular weight of 1100 Daltons). The hydroxyl groups on the polymer ends can react with the surface hydroxyl groups of the fumed silica causing the silica to become less flowable.

Adhesion Promoters

Suitable adhesion promoters can also be included in the polymerizable composition to increase the bond strength of the adhesive (polymerizable composition or seal) to the substrate (skin) or tissue as curing occurs. Tetrapropoxysilane is an exemplary adhesion promoter commonly used in silicone primers. Without wishing to be bound by any particular theory, the applicant contemplates that the reactive silane may form hydrogen or even covalent bonds with the skin. The adhesion promoter(s), when included in the polymerizable composition, can comprise between 0.01-20 wt %, between 0.01-10 wt %, between 0.1 and 5 wt %, between 0.5-5 wt %, between 1-3 wt %, between 0.1-2 wt %, and more preferably between 0.4 and 1.2 wt % (e.g., 0.8 wt %) of the polymerizable composition.

Additional adhesion promoters suitable for contemplated polymerizable formulations include those shown in Table 1. Equal parts of the first and second components including the different adhesion promoters were mixed and a thin layer was applied to a forearm and allowed to vulcanize at room temperature. The samples were evaluated by recording the time that the edges began to lift from the skin. Once the edges lifted, the samples were peeled off and evaluated qualitatively for how difficult it was to peel complete off the skin. Each adhesion promoter was evaluated, and the results are described in Table 1 below. All percentages used herein are weight percentages (wt %) unless otherwise indicated.

TABLE 1

| Formulation | Edge Lifting Began | Adhesion to skin |
|---|---|---|
| Formulation of table 2 with no adhesion promoter | 1 hour | poor |
| Formulation of table 2 with 1% 3-aminopropyltrimethoxysilane | 3.25 hours | good |
| Formulation of table 2 with 1.5% 3-aminopropyltrimethoxysilane | 3.25 hours | good |
| Formulation of table 2 with 1.5% 3-aminopropyltrimethoxysilane and 0.25% N-(triethoxysilylpropyl)-O-polyethylene oxide urethane | 3.5 hours | good |
| Formulation of table 2 with 1% Tris(2-methoxyethoxy)(vinyl)silane | 2 hours | poor |
| Formulation of table 2 with 1.5% Tris(2-methoxyethoxy)(vinyl)silane | 2.5 hours | poor |
| Formulation of table 2 with 1.5% Tris(2-methoxyethoxy)(vinyl)silane and 0.25% N-(triethoxysilylpropyl)-O-polyethylene oxide urethane | 2 hours | poor |
| Formulation of table 2 with 1% Vinyltriethoxysilane | 2 hours | poor |

TABLE 1-continued

| Formulation | Edge Lifting Began | Adhesion to skin |
|---|---|---|
| Formulation of table 2 with 1.5% Vinyltriethoxysilane | 2.5 hours | poor |
| Formulation of table 2 with 1.5% Vinyltriethoxysilane and 0.25% N-(triethoxysilylpropyl)-O-polyethylene oxide urethane | 2.25 hours | poor |
| Formulation of table 2 with 1% Tetrakis(2-methoxyethyl)ester | 4 hours | good |
| Formulation of table 2 with 1% Tetrakis(2-methoxyethyl)ester | 4 hours | good |
| Formulation of table 2 with 1.5% Tetrakis(2-methoxyethyl)ester | 4 hours | good |
| Formulation of table 2 with 1.5% Tetrakis(2-methoxyethyl)ester and 0.25% N-(triethoxysilylpropyl)-O-polyethylene oxide urethane | 3 hours | good |
| Formulation of table 2 with 1% Trimethoxy-7-octenylsilane | 5 hours | good |
| Formulation of table 2 with 1% Trimethoxy-7-octenylsilane | 5 hours | good |
| Formulation of table 2 with 1.5% Trimethoxy-7-octenylsilane | 5 hours | good |
| Formulation of table 2 with 1.5% Trimethoxy-7-octenylsilane and 0.25% N-(triethoxysilylpropyl)-O-polyethylene oxide urethane | 6 hours | good |
| Formulation of table 2 with 0.25% N-(triethoxysilylpropyl)-O-polyethylene oxide urethane | 6.5 hours | good |
| Formulation of table 2 with 0.5% N-(triethoxysilylpropyl)-O-polyethylene oxide urethane | 6.5 hours | good |
| Formulation of table 2 with 1.5% 3-glycidoxypropyltrimethoxysilane | 8 hours | Very good |
| Formulation of table 2 with 1.5% 3-glycidoxypropyltrimethoxysilane and 0.25% N-(triethoxysilylpropyl)-O-polyethylene oxide urethane | 9 hours | Very good |
| Formulation of table 2 with 1% Tetrapropoxysilane | 5 hours | good |
| Formulation of table 2 with 1.5% Tetrapropoxysilane | 5 hours | good |
| Formulation of table 2 with 0.25% N-(triethoxysilylpropyl)-O-polyethylene oxide urethane and 1.5% Tetrapropoxysilane | 18 hours | Excellent (synergistic effect with respect to adhesion where two adhesion promoters were used) |

As shown in Table 1 above, Applicant surprisingly discovered that formulations including a combination of N-(triethoxysilylpropyl)-O-polyethylene oxide urethane and Tetrapropoxysilane showed synergistic effects with respect to adhesion strength and adhesion time of the formed film to skin. More specifically, while compositions including 0.25% N-(triethoxysilylpropyl)-O-polyethylene oxide urethane began lifting after 6.5 hours, and compositions including 1.5% Tetrapropoxysilane began lifting after 5 hours, compositions including both 1.5% Tetrapropoxysilane and 0.25% N-(triethoxysilylpropyl)-O-polyethylene oxide urethane did not begin to lift for 18 hours, and had an "excellent" adhesion to skin. In contrast, when N-(triethoxysilylpropyl)-O-polyethylene oxide urethane was used in combination with other adhesion promoters, synergistic effects were not found, and only moderate changes in lift time were found (e.g., ±1 hour).

It is contemplated that the combination of at least two adhesion promoters can increase at least one of an adhesion time and an adhesion strength of the film or seal to the skin by at least 5%, more preferably at least 10%, at least 15%, at least 20%, at least 30%, at least 40%, or even at least 50% or more when compared to one of the two or more adhesion promoters alone as present in the same concentration as the combination of the at least two adhesion promoters. Additionally or alternatively, the film formed by a polymerizable composition having at least two adhesion promoters in synergistic amounts can have an edge that entirely adheres to the skin for at least 6 hours, at least 12 hours, at least 15 hours, or even at least 18 hours under normal conditions. As used herein, the term "an edge that entirely adheres to skin" means that all edges of the film remains adhered to the skin without any edge portion lifting. As used herein, the term "normal conditions" should be interpreted broadly to include stretching and flexing of the user's skin (e.g., in connection with walking, exercising, working) without any direct application of force to the film. It is also contemplated that the film formed can entirely adhere to the skin for at least 1 hour, at least 3 hours, at least 6 hours, at least 12 hours, at least 15 hours, or even at least 18 hours even when direct force is applied to the film (e.g., when showering, bathing, rubbing, swimming).

The formulation used in each of the formulations of Table 1 are shown in Table 2. The adhesion promoter(s) of Table 1 were added to Part 2 of the formulation, and equal amounts of Parts 1 and 2 were mixed. However, it should be appreciated that the adhesion promoter could alternatively or additionally be added to Part 1 of the formulation. It should also be appreciated that the percentages shown in Part 2 below are modified once the adhesion promoter(s) are added.

strength, the elongation at break, and tear resistance. Viewed from another perspective, the pigments or colorants will not change the hardness, the tensile strength, the elongation at break or tear resistance by more than 10%, more preferably not more than 5%.

Radio-Opaque Particles

Radio opaque or other particles (e.g., barium sulfate, zirconium dioxide) could be suspended or otherwise incorporated into the polymerizable formulations such that the cured seal can be detected by X-ray, computed tomography scans, ultrasound imaging or MRI scans. In some preferred embodiment, at least 2 wt %, at least 5 wt %, more preferably at least 8 wt % (e.g., between 1-50 wt %, between 8-50 wt %, between 5-30 wt %, between 8-10 wt %, between 10-20 wt %) is included in the combined two part polymerizable formulation for detection by X-ray. The radio opaque particles could be added to the polymerizable formulation in any commercially suitable matter, and could even be pre-mixed with one or more of its components. For example, the radio opaque particles could be mixed in with the first formulation component, second formulation component, silicone polymer, platinum catalyst, cross-linker, adhesion promoter, cure inhibitor, filler, thixotropic agent, or any combination thereof.

Seal/Film

It is contemplated that the first and second formulations can react with each other at various temperatures, including for example at temperatures between −20 and 80 degrees Celsius, more typically between 0 and 60 degrees Celsius, and even more typically between 10 and 50 degrees Celsius. For example, it is contemplated that the formulations will be capable of reacting together to form a seal at room tempera-

TABLE 2

| Part 1 | | Part 2 | |
|---|---|---|---|
| Component | Wt % | Component | Wt % |
| Vinyl endblocked polydimethyl siloxane polymer | 79.95 ± 5 | Vinyl endblocked polydimethyl siloxane polymer | 76.985 ± 5 |
| Fumed silica with surface area of 200 m²/gram | 19.99 ± 2 | Fumed silica with surface area of 200 m²/gram | 19.2 ± 2 |
| Platinum catalyst complex | 0.06 ± .3 | Trimethyl endblocked methyl-hydrogen siloxane polymer cross-linker (containing 50% methyl hydrogen and 50% dimethyl) | 3.8 ± 1 |
| | | 1,3,5,7-tetramethyl-1,3,5,7-tetravinyl-cyclotetrasiloxane | 0.015 ± .005 |

Pigments

It is also contemplated that inert pigments can be suspended in the polymerizable formulations without leaching into the wound or body. Suitable uses for inert pigments can include visibility, aesthetics (e.g., with designs), identification, or camouflaging (e.g., flesh tones, bright tones, or any other suitable tones). Some contemplated powdered pigments can advantageously be broken down to a size of less than 20 microns, more preferably less than 15 microns to allow for even distribution or dispersion throughout the polymerizable formulation. Additionally or alternatively, concentrated liquid or gum color pigments can be added to one or more components of the polymerizable formulation.

Pigments or colorants can be included in the polymerizable composition at between 0.001-10 wt %, between 0.01-6 wt %, or in any other suitable amount. Preferably, the pigments will not substantially negatively affect the physical properties of the polymerizable composition or the film formed, including for example, the hardness, the tensile ture (20±5° C.) and atmospheric pressure, or advantageously in the presence of a catalyst, by a hydrosilylation reaction or a condensation reaction, or a crosslinking reaction in the presence of a peroxide.

A complete seal can be formed within 20 minutes, within 10 minutes, more preferably within five minutes, within three minutes, within two minutes, or even within one minute. The seal can have any suitable thickness to treat or manage the injury, for example a thickness of between 0.1 mm and 50 mm, between 1 mm and 40 mm, between 1 mm and 20 mm, between 1 mm and 10 mm, or between 1 mm and 5 mm.

Upon full curing, the seal can have a hardness sufficient to prevent unwanted flowing of the seal. For example, the seal can have a hardness of at least 10 on the Shore 00 durometer scale, at least 10 on the Shore A scale, a hardness of between 0 on the Shore 00 durometer scale and 40 on the Shore A durometer scale, a hardness of between 10 on the Shore 00 durometer scale and 30 on the Shore A durometer scale, a hardness of between 15-25 on the Shore A durometer scale, or a hardness of between 18-22 on the Shore A durometer scale. The work time of the polymerizable composition can be approximately half of the cure time (e.g., about sixty seconds where the cure time is about two minutes).

Additionally or alternatively, the seal can have an elasticity that allows for movement and stretching of the body without compromising the seal or causing discomfort or pain. For example, some contemplated compositions will have an elongation at break of at least 200%, more preferably at least 300%, and more preferably at least 400% (e.g., between 200-1000%, between 400 and 800%, between 450-600%). As used herein, the term "% elongation at break" refers to the extension of a length of a cured seal from an unstretched and normal configuration before tearing, at room temperature, wherein the cured seal has a thickness of between 3-5 mm in the unstretched, normal configuration. For example, where a cured seal has an at least 180% elongation at break, the cured seal, when normally having a thickness of between 3-5 mm, can be stretched to at least 180% of its length before tearing (e.g., from 10 mm to at least 18 mm before tearing). Viewed from a different perspective, the seal can have a tensile strength that allows significant force to be applied while maintaining its integrity (e.g., between 100-2000 psi, between 200-800 psi, between 400-650 psi).

Still further, in some embodiments, the seal or film can have a leather adhesive force of at least 50 N/mm, at least 60 N/mm, at least 70 N/mm, at least 80 N/mm, at least 90 N/mm, at least 100 N/mm, or at least 125 N/mm when a layer between 3-5 mm of a contemplated polymerizable composition is applied to and sandwiched between two strips of soft flexible leather at room temperature, set for 30 minutes, and peeled at a 180 degree angle at a rate of 10 mm/s.

Examples

Multi-Component Polymerizable Compositions

Table 3 shows an exemplary two part polymerizable formulation having a dual adhesion promoter system. The two adhesion promoters work synergistically to increase adhesion to skin when compared to formulations having only one of the adhesion promoters. Without wishing to be bound by any particular theory, Applicant contemplates that one adhesion promoter makes the second more available at the surface of the formulation. Although the two adhesion promoters in this example are provided in Part 2 of the formulation, it should be appreciated that one adhesion promoter could be provided in each of Parts 1 and 2, that both adhesion promoters could be provided in Part 1, or that one adhesion promoter could be provided in the polymerizable formulations while a second adhesion promoter is provided in a base composition.

The formulation of Table 1 has a working time of between 20-40 seconds (typically about 30 seconds), and a setting time of between 4-6 minutes (typically about 5 minutes) when Part 1 and Part 2 are mixed together and placed on skin.

TABLE 3

| Part 1 | | Part 2 | |
| --- | --- | --- | --- |
| Component | Wt % | Component | Wt % |
| Vinyl endblocked polydimethyl siloxane polymer (chain length 350 repeating units) | 79.947 | Vinyl endblocked polydimethyl siloxane polymer (chain length 350 repeating units) | 74-75 |
| Fumed silica with surface area of 200 m$^2$/gram | 19.91 | Fumed silica with surface area of 200 m$^2$/gram | 18.5-19 |
| Platinum catalyst complex | 0.143 | Trimethyl endblocked methylhydrogen siloxane polymer crosslinker (containing 50 wt % methyl hydrogen and 50 wt % dimethyl) | 3.5-4.0 |
| | | 1,3,5,7-tetramethyl-1,3,5,7-tetravinyl-cyclotetrasiloxane | 0.013-0.017 |
| | | Tetrapropoxysilane adhesion promoter | 2.2-2.8 |
| | | N-(triethoxysilylpropyl)-O-polyethylene oxide urethane adhesion promoter | 0.37-0.45 |

It is also contemplated that the components shown in Table 1 could be included in Part 1 and Part 2 of the formulation in different concentration ranges as set forth below in Table 4 with comparable work times (e.g., between 10-120 seconds), setting times (e.g., between 1-10 minutes), adhesion properties (as described in Table 1), hardness of between 5-80 on the ShoreA hardness scale, tensile strength between 200-1500 psi, and elongation at break (of between 200-1000%).

TABLE 4

| Part 1 | | Part 2 | |
| --- | --- | --- | --- |
| Component | Wt % | Component | Wt % |
| Vinyl endblocked polydimethyl siloxane polymer (100-1000 DP) | 60-90 | Vinyl endblocked polydimethyl siloxane polymer (100-1000 repeating siloxy units) | 60-90 |
| Fumed silica with surface area of 200 $m^2$/gram (100-400 $m^2$/gram) | 10-30 | Fumed silica with surface area of 200 $m^2$/gram | 10-30 |
| Platinum catalyst complex | 0.06-0.2 | Trimethyl endblocked methyl-hydrogen siloxane polymer cross-linker (containing 50% methyl hydrogen and 50% dimethyl) | 2-10 |
| | | 1,3,5,7-tetramethyl-1,3,5,7-tetravinyl-cyclotetrasiloxane | .001-.05 |
| | | Tetrapropoxysilane adhesion promoter | 1-5 |
| | | N-(triethoxysilylpropyl)-O-polyethylene oxide urethane adhesion promoter | 0.1-2 |

Table 5 shows an exemplary formulation including barium sulfate, which is contemplated to have comparable work times (e.g., between 10-120 seconds), setting times (e.g., between 1-10 minutes), adhesion properties, hardness, tensile strength, and elongation at break as the formulation of Table 1.

TABLE 5

| Part 1 | | Part 2 | |
| --- | --- | --- | --- |
| Component | Wt % | Component | Wt % |
| Vinyl endblocked polydimethyl siloxane polymer | 66.6 ± 20 | Vinyl endblocked polydimethyl siloxane polymer | 74.9 ± 20 |
| Fumed silica with surface area of 200 $m^2$/gram | 16.7 ± 10 | Fumed silica with surface area of 200 $m^2$/gram | 18.7 ± 10 |
| Platinum catalyst complex | 0.05 (0.001-0.2) | Trimethyl endblocked methyl-hydrogen siloxane polymer cross-linker (containing 50% methyl hydrogen and 50% dimethyl) | 3.7 ± 3 |
| Barium Sulfate (to make the formulation radio-opaque) | 16.7 ± 15 | 1,3,5,7-tetramethyl-1,3,5,7-tetravinyl-cyclotetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Table 6 shows an exemplary formulation including one or more pigments, which is contemplated to have comparable work times (e.g., between 10-90 seconds), setting times (e.g., between 1-10 minutes), adhesion properties, and elongation at break as the formulation of Table 1.

TABLE 6

| Part 1 | | Part 2 | |
|---|---|---|---|
| Component | Wt % | Component | Wt % |
| Vinyl endblocked polydimethyl siloxane polymer | 78.4 ± 20 | Vinyl endblocked polydimethyl siloxane polymer | 74.9 ± 20 |
| Fumed silica with surface area of 200 m²/gram | 19.6 ± 10 | Fumed silica with surface area of 200 m²/gram | 18.7 ± 10 |
| Platinum catalyst complex | 0.06 (0.001-0.2) | Trimethyl endblocked methyl-hydrogen siloxane polymer cross-linker (containing 50% methyl hydrogen and 50% dimethyl) | 3.7 ± 3 |
| Pigment (e.g., yellow, orange, green, blue, brown) | 1.96 ± 1.5 | 1,3,5,7-tetramethyl-1,3,5,7-tetravinyl-cyclotetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Tables 7-10 show exemplary formulations only including one adhesion promoter, which is contemplated to have comparable work times (e.g., between 10-90 seconds), setting times (e.g., between 1-10 minutes), hardness, tensile strength, and elongation at break as the formulation of Table 1, but a lower adhesion strength to skin likely due to a lack of synergistic effect with a second adhesion promoter.

TABLE 7

| Part 1 | | Part 2 | |
|---|---|---|---|
| Component | Wt % | Component | Wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 m²/gram | 19.99 ± 10 | Fumed silica with surface area of 200 m²/gram | 18.8 ± 10 |
| Platinum catalyst complex | 0.06 (0.001-0.2) | Trimethyl endblocked methyl-hydrogen siloxane polymer cross-linker (containing 50% methyl hydrogen and 50% dimethyl) | 3.8 ± 3 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.3 ± 2 |

TABLE 8

| Part 1 | | Part 2 | |
|---|---|---|---|
| Component | Wt % | Component | Wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 m²/gram | 19.99 ± 10 | Fumed silica with surface area of 200 m²/gram | 18.8 ± 10 |
| Platinum catalyst complex | 0.06 (0.001-0.2) | Trimethyl endblocked methyl-hydrogen siloxane polymer cross-linker (containing 50% methyl hydrogen and 50% dimethyl) | 3.8 ± 3 |
| | | 1,3,5,7-tetramethyl-1,3,5,7-tetravinyl-cyclotetrasiloxane | 0.015 (between 0.001-0.05) |
| | | N-(triethoxysilylpropyl)-O-polyethylene oxide urethane adhesion promoter | 0.37 (0.1-2) |

TABLE 9

| Part 1 | | Part 2 | |
| --- | --- | --- | --- |
| Component | Wt % | Component | Wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 m$^2$/gram | 19.99 ± 10 | Fumed silica with surface area of 200 m$^2$/gram | 18.8 ± 10 |
| Platinum catalyst complex | 0.06 (0.001-0.2) | Trimethyl endblocked methyl-hydrogen siloxane polymer cross-linker (containing 50% methyl hydrogen and 50% dimethyl) | 3.8 ± 3 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.57 ± 2.5 |

TABLE 10

| Part 1 | | Part 2 | |
| --- | --- | --- | --- |
| Component | Wt % | Component | Wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 m$^2$/gram | 19.99 ± 10 | Fumed silica with surface area of 200 m$^2$/gram | 18.8 ± 10 |
| Platinum catalyst complex | 0.06 (0.001-0.2) | Trimethyl endblocked methyl-hydrogen siloxane polymer cross-linker (containing 50% methyl hydrogen and 50% dimethyl) | 3.8 ± 3 |
| | | 1,3,5,7-tetramethyl-1,3,5,7-tetravinyl-cyclotetrasiloxane | 0.015 (between 0.001-0.05) |
| | | N-(triethoxysilylpropyl)-O-polyethylene oxide urethane adhesion promoter | 2.57 ± 2.5 |

Table 11 shows an exemplary formulation including a thixotropic agent added to make the formulation non-slump at a concentration of between 0.25-3 wt %. The formulation of Table 10 is contemplated to have comparable work times (e.g., between 10-90 seconds), setting times (e.g., between 1-10 minutes), adhesion properties, hardness, tensile strength, and elongation at break as the formulation of Table 1.

TABLE 11

| Part 1 | | Part 2 | |
| --- | --- | --- | --- |
| Component | Wt % | Component | Wt % |
| Vinyl endblocked polydimethyl siloxane polymer | 79.32 ± 20 | Vinyl endblocked polydimethyl siloxane polymer | 74.9 ± 20 |
| Fumed silica with surface area of 200 m$^2$/gram | 19.83 ± 10 | Fumed silica with surface area of 200 m$^2$/gram | 18.7 ± 10 |
| Platinum catalyst complex | 0.06 (0.001-0.2) | Trimethyl endblocked methyl-hydrogen siloxane polymer cross-linker (containing 50% methyl hydrogen and 50% dimethyl) | 3.7 ± 3 |
| Hydroxyl endblocked polydimethyl siloxane (thixotrope) | 0.79 (between 0.25-3) | 1,3,5,7-tetramethyl-1,3,5,7-tetravinyl-cyclotetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Table 12 shows another exemplary formulation including less platinum catalyst than the formulation of Table 1, which is contemplated to require a longer cure time.

TABLE 12

| Part 1 | | Part 2 | |
| --- | --- | --- | --- |
| Component | Wt % | Component | Wt % |
| Vinyl endblocked polydimethyl siloxane polymer | 79.97 ± 20 | Vinyl endblocked polydimethyl siloxane polymer | 74.9 ± 20 |
| Fumed silica with surface area of 200 m²/gram | 19.99 ± 10 | Fumed silica with surface area of 200 m²/gram | 18.7 ± 10 |
| Platinum catalyst complex | 0.04 (0.001-0.2) | Trimethyl endblocked methyl-hydrogen siloxane polymer cross-linker (containing 50% methyl hydrogen and 50% dimethyl) | 3.7 ± 3 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Table 13 shows another exemplary formulation including less cross-linker than the formulation of Table 1, which is contemplated to require a longer cure time.

TABLE 13

| Part 1 | | Part 2 | |
| --- | --- | --- | --- |
| Component | Wt % | Component | Wt % |
| Vinyl endblocked polydimethyl siloxane polymer | 79.95 ± 20 | Vinyl endblocked polydimethyl siloxane polymer | 76 ± 20 |
| Fumed silica with surface area of 200 m²/gram | 19.997 ± 10 | Fumed silica with surface area of 200 m²/gram | 79 ± 10 |
| Platinum catalyst complex | 0.06 (0.001-0.2) | Trimethyl endblocked methyl-hydrogen siloxane polymer cross-linker (containing 50% methyl hydrogen and 50% dimethyl) | 2.3 ± 2 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.3 ± 2 |
| | | N-(triethoxysilylpropyl)-O-polyethylene oxide urethane adhesion promoter | 0.38 (0.1-2) |

Applicant surprisingly discovered that the cured seal of some compositions discussed above had some properties stronger than skin, as a suture would not pull through the cured seal with the same strength applied to pull a suture through skin.

Table 14 shows another exemplary formulation including no fumed silica.

TABLE 14

| Part 1 | | Part 2 | |
| --- | --- | --- | --- |
| Component | Wt % | Component | Wt % |
| Vinyl endblocked polydimethyl siloxane polymer | 99.93 | Vinyl endblocked polydimethyl siloxane polymer | 92.1 ± 20 |
| Platinum catalyst complex | 0.07 (0.001-0.2) | Trimethyl endblocked methyl-hydrogen siloxane polymer cross-linker (containing 50% methyl hydrogen and 50% dimethyl) | 4.6 ± 4 |

TABLE 14-continued

| Part 1 | | Part 2 | |
|---|---|---|---|
| Component | Wt % | Component | Wt % |
| | | 1,3,5,7-tetramethyl-1,3,5,7-tetravinyl-cyclotetrasiloxane | 0.018 (between 0.001-0.05) |
| | | Tetrapropoxysilane adhesion promoter | 2.8 ± 2 |
| | | N-(triethoxysilylpropyl)-O-polyethylene oxide urethane adhesion promoter | 0.46 (0.1-2) |

Tables 15 and 16 show other exemplary compositions that can be used for some of the uses described herein, although the compositions would not have the adhesion strength or time of some of the above-referenced formulations.

TABLE 15

| Part 1 | | Part 2 | |
|---|---|---|---|
| Component | Wt % | Component | Wt % |
| Polydimethyl siloxane polymer | 18-45 | Polydimethyl siloxane polymer | 18-45 |
| Silicone dioxide, non-crystalline | 3-13 | Silicone dioxide, non-crystalline | 3-13 |
| Platinum catalyst | 0.02-2 | Methyl hydrogen polysiloxane cross-linker | 2-12 |
| Cyclopentasiloxane | 0.01-1 | Methyl vinyl inhibitor | 0.01-2 |
| Hydroxyl terminated polymethylphenylsiloxane | 0.01-1 | Fumed silica | 0.01-5 |
| Dimethicone | 0.01-2 | Cyclopentasiloxane | 0.01-2 |
| Silicone oil | 0.01-3 | Dimethicone | 0.01-2 |
| | | Hydroxyl terminated polymethylphenylsiloxane | 0.01-2 |
| | | *Boswellia Serrata* extract | 0.01-1 |
| | | Green tea powder | 0.01-1 |

TABLE 16

| Part 1 | | Part 2 | |
|---|---|---|---|
| Component | Wt % | Component | Wt % |
| Polydimethyl siloxane polymer | 10-38 | Polydimethyl siloxane polymer | 10-38 |
| Silicone dioxide, non-crystalline | 3-12 | Silicone dioxide, non-crystalline | 3-12 |
| Platinum catalyst | 0.1-1 | Methyl hydrogen polysiloxane cross-linker | 2-10 |
| Cyclopentasiloxane | 0.01-.05 | Methyl vinyl inhibitor | 0.01-1 |
| Hydroxyl terminated polymethylphenylsiloxane | 0.01-.05 | Fumed silica | 0.01-2 |
| Dimethicone | 0.01-1 | Cyclopentasiloxane | 0.01-1 |
| Silicone oil | 0.01-2 | Dimethicone | 0.01-1 |
| | | Hydroxyl terminated polymethylphenylsiloxane | 0.01-1 |
| | | *Boswellia Serrata* extract | 0.01-5 |
| | | Green tea powder | 0.01-5 |

Exemplary formulations can also be viewed from a parts-per-hundred (pph) perspective. In Tables 17-19, all components are based on 100 parts of NuSil MED-4220 Part A or Part B (e.g., NuSil MED2-4220). Therefore, in order to add 3 pph of a component to 100 grams NuSil MED4220 Part A, 3 grams of the component would be added.

Table 17 shows an exemplary formulation having a working time of between 20-40 seconds (typically about 30 seconds), and a setting time of between 4-6 minutes (typically about 5 minutes) when Part 1 and Part 2 are mixed together and placed on skin.

TABLE 17

| Part 1 | | Part 2 | |
|---|---|---|---|
| Component | pph | Component | pph |
| NuSil MED4220 Part A | 100 | NuSil MED4220 Part B | 100 |
| NuSil CAT-50 | 0.01-0.30 (e.g., 0.09) | NuSil XL-100 | 0.5-5 (e.g., 1.5-2.5, or 2.0) |

TABLE 17-continued

| Part 1 | | Part 2 | |
| --- | --- | --- | --- |
| Component | pph | Component | pph |
| | | Gelest SIT 7777.0 | 0.5-6.0 (e.g., 2.0-4.0, or 3.0) |
| | | Gelest SIT 8192.0 | 0.01-1.0 (e.g., 0.5) |

Table 18 shows an exemplary formulation including radio-opaque particles for detection by X-ray.

TABLE 18

| Part 1 | | Part 2 | |
| --- | --- | --- | --- |
| Component | pph | Component | pph |
| NuSil MED4220 Part A | 100 | NuSil MED4220 Part B | 100 |
| NuSil MED2-4800 | 10.0-100.0 (e.g., 20.0-60.0, or 40.0) | NuSil XL-100 | 0.5-5 (e.g., 1.5-2.5, or 2.0) |
| NuSil CAT-50 | 0.01-0.30 (e.g., 0.1) | Gelest SIT 7777.0 | 0.5-6.0 (e.g., 2.0-4.0, or 3.0) |
| | | Gelest SIT 8192.0 | 0.01-1.0 (e.g., 0.5) |

Table 19 shows an exemplary formulation including pigments for, among other things, visibility, aesthetics (e.g., with designs), identification, or camouflaging (e.g., flesh tones, bright tones, or any other suitable tones).

TABLE 19

| Part 1 | | Part 2 | |
| --- | --- | --- | --- |
| Component | pph | Component | pph |
| NuSil MED4220 Part A | 100 | NuSil MED4220 Part B | 100 |
| NuSil MED2-4800 | 10.0-100.0 (e.g., 20.0-60.0, or 40.0) | NuSil XL-100 | 0.5-5 (e.g., 1.5-2.5, or 2.0) |
| NuSil CAT-50 | 0.01-0.30 (e.g., 0.1) | Gelest SIT 7777.0 | 0.5-6.0 (e.g., 2.0-4.0, or 3.0) |
| NuSil MED-4800-5 | 1.0-10.0 (e.g., 3.0-7.0, or 5.0) | Gelest SIT 8192.0 | 0.01-1.0 (e.g., 0.5) |

The PHOSITA should appreciate that the ingredients described herein can be obtained from different commercial suppliers. For example, it is contemplated that components of some contemplated polymerizable compositions or base component can be obtained from commercial suppliers, for example, Silbond Corporation, Chemat, H. W. Sands Corp., Fluorochem USA, Gelest, Inc., Dupont Performance chemicals, Nusil Technology, Power Chemical Corporation, Rhodia Silicones, Reliance Silicones, or Zentek.

Base Compositions

Where one or more base compositions are applied to the injury, for example prior to applying the polymerizable composition that forms a seal, such base compositions could comprise at least one of an anesthetic, an antiseptic, an adhesion promoter, an antipruritic, a catalyst, a haemostatic agent, a vitamin, a botanical, a drug, and a vasoconstrictor. Viewed from another perspective, the base composition could advantageously provide one or more of a pain relieving, therapeutic, antimicrobial, or blood coagulative effect. Additionally or alternatively, the base composition could act as or include a primer that promotes adhesion of the polymerizable composition to the skin or tissue when applied, and include a catalyst to decrease the cure time at the wound edges of the polymerizable composition. Preferably, the base composition will not negatively impact the polymerizable composition's ability to adhere to the skin or tissue, or to cure in situ in a short amount of time.

Contemplated local anesthetics include, among others, xylocaine, lidocaine, lignocaine, bupivacaine, benzocaine, tetracaine (amethocaine), ropivacaine, prilocaine, procaine, cinchocaine, mepivacaine and etidocaine. Each local anesthetic (or the combination of anesthetics) can be present in the base composition in any suitable amount. For example, it is contemplated that the local anesthetic can be present in a spray, ointment, jelly or other composition in any suitable concentration, including for example, a concentration of between 1-500 mg/ml, between 1-250 mg/ml, between 5-100 mg/ml, or between 5-50 mg/ml. If the local anesthetic (or other base ingredient) is included in the polymerizable composition, for example instead of or in addition to the base, it is contemplated that the same, lower or higher concentration of the local anesthetic could be included.

Contemplated antiseptics include benzalkonium chloride, tea tree oil, alcohol, hydrogen peroxide, iodine, and boric acid. Each antiseptic (or the combination of antiseptics) can be present in the base composition in any suitable amount. For example, it is contemplated that the antiseptic can be present in the base (e.g., a spray, ointment, jelly, other composition) in any suitable concentration, including for example, a concentration of between 0.1-100 mg/ml, between 0.1-50 mg/ml, between 0.1-10 mg/ml, between 0.1-5 mg/ml, or between 0.8-1.8 mg/ml. Viewed from a different perspective, the antiseptic can be present in the base composition at a concentration of between 0.01-1.0 w/w %, between 0.01-0.5 w/w %, or between 0.08-0.18 w/w %.

Contemplated adhesion promoters can include a silane coupling agent containing one or more functional groups that bond with the polymerizable composition or components thereof. Some contemplated adhesion promoters include a tetramethoxysilane, a tetraethoxysilane, a tetraisopropoxysilane, a tetrapropoxysilane, a tetrabutoxysilane, a tetraacetoxysilane, a 3-aminopropropyltrimethoxysilane, tris(2-methoxyethoxy)(vinyl)silane, vinyltriethoxysilane, tetrakis(2-methoxyethyl)ester, and trimethoxy-7-octenylsilane. An adhesion promoter where included in the base composition can be the same as or different from the adhesion promoter(s) included in a polymerizable composition. Additionally or alternative, the base composition could comprise one adhesion promoter of a synergistic pair, while the polymerizable composition could comprise another adhesion promoter of the synergistic pair.

When included, the adhesion promoter(s) can be present in the base composition in any suitable amount. For example, it is contemplated that the adhesion promoter can be present in a spray, ointment, jelly, powder or other type of base composition in any suitable concentration, including for example, a concentration of between 0.1-100 mg/ml, between 0.1-75 mg/ml, between 0.1-50 mg/ml, between 0.1-10 mg/ml, or between 0.5-10 mg/ml.

Vasoconstrictors can be included in contemplated base compositions, and can have several beneficial effects, for example, when added to a local anesthetic. For example, the vasoconstrictor can decrease the peak plasma concentration of the local anesthetic agent, increase the duration and quality of the anesthesia, reduce the minimum concentration of anesthetic needed for nerve blocking, and decrease the amount of blood lost. Contemplated vasoconstrictors include epinephrine, norepinephrine, vasopressin, oxymetazoline, phenylephrine, anhydrous aluminum sulfate, and pseudoephedrine.

When included, the vasoconstrictor(s) can be present in the base composition in any suitable amount. For example, it is contemplated that the vasoconstrictor can be present in a spray, ointment, jelly or other type of base composition in any suitable concentration, including for example, a concentration of between 0.1-100 mg/ml, between 0.1-75 mg/ml, between 0.1-50 mg/ml, between 0.1-10 mg/ml, or between 0.5-10 mg/ml.

All suitable antipuritic components are contemplated, and can include antihistamines such as diphenhydramine, corticosteroids such as hydrocortisone, menthol, camphor, or a local anesthetic (e.g., lidocaine, pramoxine, benzocaine). When included, the antipuritic component(s) can be present in the base composition in any suitable amount. For example, it is contemplated that the antipuritic can be present in a spray, ointment, jelly or other composition in any suitable concentration, including for example, a concentration of between 1-500 mg/ml (0.1-50%), between 1-100 mg/ml (0.1-10%), or between 1-50 mg/ml (0.1-5%).

A haemostatic agent could also be included in contemplated base compositions to slow down or stop a bleed when applied directly on the source. Some exemplary haemostatic agents include antifibrinolytics, blood coagulation factors, fibrinogen, vitamin K, microfibrillar collagen hemostat (MCH), chitosan hemostats, and thromboplastin.

Similarly to the polymerizable composition, the base composition can also include a silicone or other catalyst that promotes curing of the polymerizable composition, which can be present in any suitable concentration (e.g., between 0.001-50 mg/ml). A catalyst included in the base composition could be the same as or different from one or more catalysts included in the polymerizable formulation.

In some embodiments, botanicals can be included in the base composition, including for example, plant extracts (e.g., chamomile extract, gotu kola extract, *Boswellia serrata* extract, green tea extract) or other active components of plants (e.g., curcumin). For example, the plant extract(s) can be included at between 0.01-20 wt %, more preferably less than 10 wt %, and even more preferably less than 5 wt %.

Exemplary primer base compositions (e.g., gel, liquid, spray) can comprise one or more reactive silanes, a catalyst, and a solvent carrier (among other things). The reactive silanes can include a reactive group that is compatible with the polymerizable composition, and another reactive group that is compatible with the substrate (e.g., skin, tissue) to thereby promote adhesion of the polymerizable composition to the substrate. One exemplary silicone primer comprises between 88-93 wt % isopropyl alcohol (e.g., 88 wt %), between 1-5 wt % tetrapropoxy silane (e.g., 3%), between 1-5 wt % titanium IV butoxide (e.g., 3%), and between 0.01-2 wt % or 0.5-2 wt % of a platinum catalyst (e.g., 1 wt %). However, all suitable silicone primer compositions are contemplated.

It should be appreciated that one or more of the ingredients described above for optional inclusion in a base composition could additionally or alternatively be included in the polymerizable composition.

Other Contemplated Uses

Pre-Formed Compositions

The polymerizable compositions discussed above can be used in combination with pre-formed compositions of any suitable shape (e.g., strips, tubes), for example, to at least partially secure the pre-formed composition in place on a user's skin. All suitable pre-formed compositions of any suitable sizes, shapes and materials are contemplated, so long as they are capable of adhering to the polymerizable compositions of the inventive subject matter. For example, the pre-formed composition can include an existing object such as a tube, a strip of material, or a jewelry item or other accessory. Additionally or alternatively, the pre-formed object can be a piece of cured material that is made from the polymerizable composition, for example a pre-formed strip of material that is rolled up and can be flattened/unrolled for use. Viewed from a different perspective, custom silicone sheets or strips could be formed using the polymerizable compositions of the inventive subject matter.

One exemplary use of pre-formed materials and a polymerizable composition is to secure an oxygen nasal cannula or other tubing in place on a user's skin such that is can be safely and gently removed, even of a baby or infant's skin. Some known methods exist, typically involving taping the cannula to the user's face. Unfortunately, certain tapes can be painful to remove and even damage the user's face, while others have a weak adhesive and can easily be pulled off by the user. The preformed strip (e.g., a cured piece of the polymerizable composition) can be placed over a portion of the tubing, and small amounts of the polymerizable composition can be placed on opposite ends of the pre-formed material, and pressed upon the user's skin. The tubing would then be secured in place under the pre-formed material.

Alternatively, the cannula or other tubing could be the pre-formed material, and the polymerizable composition can be used to adhere the cannula or other tubing directly to the skin. It is contemplated that the cured polymerizable composition can adhere to various pre-formed composition for a period of at least 6 hours, a period of at least 12 hours, a period of at least 18 hours, a period of at least 1 day, a period of at least 2 days, a period of at least 3 days, or even up to one week during normal activity.

Another exemplary use of pre-formed material is as breast tape, breast lifts or pasties. As one example, a square or triangular strip of material could be adhered to a lower portion of the breast (or under the breast) using the polymerizable composition. The non-adhered end of the material could be lifted over the breast and secured to the user's skin (e.g., at the user's shoulder, collar bone, back, upper chest) once the breast is at a desired position (e.g., desired lift and cleavage). As another example, an existing breast lift could be adhered to the skin with the breast placed in the desired position. As yet another example, the pre-formed material could comprise a gel or silicone nipple cover, which can be adhered to the user's breast around the user's nipple to avoid or reduce pain from removal.

Wrinkles, Under-Eye Bags, and Other Cosmetic Uses

The polymerizable compositions of the inventive subject matter could also be used to camoflauge or treat wrinkles, under-eye bags, or any other portion of the skin where greater skin elasticity is desired. The user's skin could be stretched to reduce the appearance of the wrinkles or the under-eye bag, and the first and second elastomer components can be mixed and applied to the stretched skin (in any suitable order). The polymerizable composition can help hold the skin in the stretched configuration to improve the appearance of the user's skin even after the cured film is removed, for example by reducing the appearance of wrinkles. In some aspects, the polymerizable composition can be applied over a treatment composition (e.g., vitamin A acid, alpha hydroxyl acids, antioxidants, moisturizers, vitamin C, retinol), or the polymerizable composition can include the treatment composition(s). In such embodiments, it is contemplated that the treatment compositions can be more effectively delivered to the user's skin as unwanted removal (e.g., on clothing, hands) can be avoided.

Tattoos

The polymerizable compositions can also be used as a post-tattoo treatment in place of an ointment and plastic wrap or other known treatments and protectors. The formed film can have edges that are adhered to the user's skin around the tattoo, and can act to seal entry points into the skin and body to prevent infections. Additionally or alternatively, the entire film can adhere to the user's skin. Where a pre-formed film or material is used, it is contemplated that the pre-formed film can be placed over an ointment or other treatment composition, and adhered to the user's skin along the edge portions such that the ointment stays in place and the pre-formed film can adhere to the skin for a longer period of time (e.g., between 1-14 days, between 1-7 days, between 1-5 days, between 1-3 days, between 2-5 days, between 2-4 days, between 2-3 days, between 3-4 days).

In some contemplated aspects, the polymerizable composition can include pigments (e.g., pigments having skin tones), which can be used to effectively cover up a tattoo for long periods of time (e.g., at least 24 hours, at least 48 hours, between 24 and 72 hours, between at least 24-48 hours) when compared to most make-up cover up formulations. The pigmented composition can be mixed and applied to the user's skin (in any other) over a tattoo to be covered up, and the film formed within five minutes can remain adhered to the skin for a period of at least 24 hours, at least 48 hours, at least 72 hours or even more. The elasticity and adhesion properties of the film allows for long term wear.

Still further, polymerizable compositions can be applied to have decorative features or designs that can be applied as a temporary tattoo.

Additional Contemplated Uses

The polymerizable compositions described herein can also be used for topical applications after a laser treatment or other cosmetic procedure (e.g., injections) to protect the treated area and decrease bruising or scarring. Additionally, Applicant contemplates use of the compositions on areas of skin affected by rosacea or other skin disorders, with or without suitable treatment compositions (e.g., metronidazole).

The compositions can also be applied as a polymerizable band-aid or skin protector that prevents or protects from picking or scratching, for example when the user suffers from allergies or excoriation disorders.

Skin bolstering uses are also contemplated, for example, to hold a flap or portion of skin in place. As one non-limiting example, the compositions can be used to push back and secure an eyelid away from the globe of the eye, or to hold a skin graft in place.

The cured compositions could also be as ear plugs, for example, to protect the ear drum from water (e.g., while swimming), from loud sounds (e.g., at concerts), and from external objects that could cause injury to the ear.

During surgical procedures, the compositions can be applied to seal an entry point of a tube or other foreign object. For example, where a chest tube or other device is entering the body (e.g., drainage tubes for breast augmentations, abdominoplasty), the polymerizable composition can be used to secure the tube in place, to seal the entry point, and to decrease the likelihood of an infection.

Other contemplated applications include, among other things, custom-made vaginal pessaries, cervical caps or diaphragms, shielding of specific areas of skin during a laser treatment or chemical peel, or to protect skin during hair dye applications, and prevention of premature suture removal, or of suture filaments grabbing onto clothing, gauze or other materials.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The discussion herein provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent, however, to those skilled in the art that many more modifications besides those already described are possible without departing from the inventive concepts herein. The inventive subject matter, therefore, is not to be restricted except in the spirit of the disclosure. One skilled in the art will recognize many methods and materials similar or equivalent to those described herein, which could be used in the practice of the present invention. Indeed, the present invention is in no way limited to the methods and materials described.

Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A method for treating a damaged or wounded skin, comprising:

mixing a first silicone-containing elastomer component with a second silicone-containing elastomer component applying substantially equal volumes of the first and second components to create an elastomer gel wherein the combination of the first and second components comprises at least two adhesion promoters present in synergistic amounts with respect to adhesion of the film to the user's skin;

wherein the at least two adhesion promoters comprises between 1-5 wt % of a tetrapropoxysilane and between 0.1-1 wt % of a N-(triethoxysilylpropyl)-O-polyethylene oxide urethane;

applying the elastomer gel on the damaged or wounded skin to form a film within ten minutes; wherein the first silicone-containing elastomer component comprises: between 0.05-0.2 wt % of a silicone platinum catalyst; between 70-90 wt % of a polydimethyl siloxane polymer;

and between 15-29.8 wt % fumed silica wherein the second silicone-containing elastomer component comprises: between 70-90 wt % of a polydimethyl siloxane polymer;

and between 15-29 wt % fumed silica; and between 1-10 wt % of a siloxane polymer cross-linker; wherein at least one of the first and second components comprises an adhesion promoter;

wherein the film has a thickness and tensile strength effective to compress the damaged or wounded skin to decrease formation of fibroblasts; and wherein the film is water resistant, provides a protective layer to the user's skin, and can be peeled off as a single piece;

wherein the film provides the protective layer to the user's skin for at least two days.

2. The method of claim 1, wherein the thickness and tensile strength of the film is effective to press blisters down.

3. The method of claim 1, wherein the thickness and tensile strength of the film is effective to decrease a biochemical cascade that promotes scar formation.

4. The method of claim 1, further comprising applying a mineral powder to the mixed first and second components, wherein the mineral powder is formulated to decrease cure time of the mixed first and second components.

5. The method of claim 4, wherein the mineral powder comprises fumed silica.

6. The method of claim 1, wherein the first and second components are formulated such that when the first and second components are applied to the user's skin and mixed, the film is formed within 5 minutes.

7. The method of claim 1, further comprising a base component prior to applying the first and second components, wherein the base component increases an adhesion of the film to the user's skin.

8. The method of claim 1, further comprising a base component prior to applying the first and second components, wherein the base component decreases a cure time of the first and second components.

* * * * *